United States Patent [19]

Hahn et al.

[11] Patent Number: 5,120,839
[45] Date of Patent: Jun. 9, 1992

[54] AMIDO-LINKED OLIGOSACCHARIDE ALDITOLS AND A PROCESS FOR THEIR MANUFACTURE

[75] Inventors: Karola Hahn, Osthofen; Bernd Schneider, Ebertsheim, both of Fed. Rep. of Germany

[73] Assignee: Suddeutsche Zucker-Aktiengesellschaft, Mannheim, Fed. Rep. of Germany

[21] Appl. No.: 540,060

[22] Filed: Jun. 19, 1990

[30] Foreign Application Priority Data

Jul. 14, 1989 [DE] Fed. Rep. of Germany ........ 3923365

[51] Int. Cl.$^5$ .............................. C07H 15/04
[52] U.S. Cl. ................... 536/17.2; 514/25; 536/17.9; 536/53; 536/4.1
[58] Field of Search ......... 536/17.2, 17.9, 53, 536/4.1; 514/25

[56] References Cited

U.S. PATENT DOCUMENTS

| | | | |
|---|---|---|---|
| 4,696,916 | 9/1987 | Yabushita et al. | 514/25 |
| 4,719,294 | 1/1988 | Rademacher et al. | 536/22 |
| 4,736,022 | 4/1988 | Rademacher et al. | 536/22 |
| 5,011,923 | 4/1991 | Ono et al. | 536/17.9 |

Primary Examiner—Ronald W. Griffin
Attorney, Agent, or Firm—Armstrong & Kubovcik

[57] ABSTRACT

The invention relates to amido-linked oligosaccharide alditols, i.e. oligosaccharide alditols with an amido linkage, having the general formula $$R_1-\overset{\overset{\displaystyle O}{\|}}{C}-\underset{\underset{\displaystyle H}{|}}{N}-R_2 \qquad (I)$$

wherein:
  $R_1$ = the alditol portion of a mono-, di- or oligosaccharide alditol, in which the alditol portion has 2 to 6 carbon atoms, and
  $R_2$ = the alditol portion of a mono-, di- or oligosaccharide alditol, in which the alditol portion has 3 to 7 carbon atoms and is combined with the terminal or another carbon atom.

They are manufactured by N-acylation of amino polyols derived from saccharides, with a sugar acid in the presence of methanol or in aprotic polar solvents.

6 Claims, No Drawings

AMIDO-LINKED OLIGOSACCHARIDE ALDITOLS AND A PROCESS FOR THEIR MANUFACTURE

TECHNICAL FIELD OF THE INVENTION

The invention relates to oligosaccharide alditols with an amido linkage, referred to hereinafter as amido oligosaccharides, having one of the formulae I, II, III, IV set forth in claim 1 and in claims 2 to 4, and to their manufacture by N-acylation, in known manner, of amino polyols derived from saccharides with sugar acids in which the acid component is activated at the carboxyl function.

SUMMARY OF THE INVENTION

Amido oligosaccharides formed by the reaction of these amino polyols with the sugar acids are a class of compound not yet described in the literature. Amido oligosaccharides have the general formula:

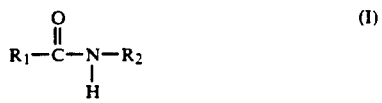

wherein:
$R_1$ = the alditol portion of a mono-, di- or oligosaccharide alditol, in which the alditol portion has 2 to 6 carbon atoms,
$R_2$ = the alditol portion of a mono-, di- or oligosaccharide alditol, in which the alditol portion has 3 to 7 carbon atoms and is linked with the terminal or another carbon atom.

The composition of the compounds that have been obtained and are claimed, having the formulae:

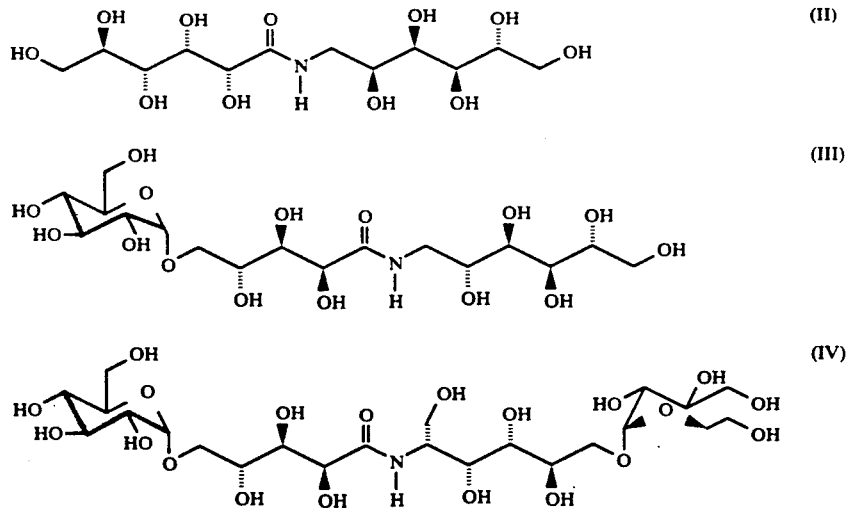

is supported by $^{13}$C-NMR-spectroscopic data.

Amino polyols, such as glucamine, mannamine, maltamine or isomaltamine, can be obtained by reductive amination of reducing mono-, di- or oligosaccharides such as glucose, mannose, fructose, sorbose, arabinose, maltose, isomaltose, maltulose, isomaltulose, trehalulose, lactose, cellobiose and higher oligosaccharides and reducing deoxy sugars, such as rhamnose and C-branched carbohydrates in ammonia or hydrazine with hydrogen using a nickel catalyst (cf. DE 35 38 451 and DE 36 25 931).

Sugar acids, e.g. gluconic acid, arabonic acid and glucopyranosyl arabonic acid, can easily be obtained by a variety of oxidizing processes from reducing carbohydrates: (cf. Monograph: J. Stanek, M. Cerny, J. Kocourek and J. Pacak, "The Monosaccharides", Academic Press, New York, 1963, p. 138.ff., and the literature quoted there, and Meth. Carbohdr. Chem. II, 11–26 (1963); Spengler, O., Pfannenstiel, A.: Z. Zuckerind. 85 (1935), 546; German Patents 618 164, 620 248 (1934); DE-OS 32 48 404, EP 0 114 954).

To react to form the amido oligosaccharide the acid component must be activated at the carboxyl function; it can, for example, be in the form of an ester, an acid halide or a lactone.

The reaction takes place in alcoholic solution (preferably methanol) or in aprotic polar solvents (preferably dimethyl formamide) at temperatures between 20° and 120° C., preferably at 60° C.

The addition products having the formula I separate in solid form from the solvent during the reaction or on cooling, and can be further purified by recrystallization.

In case a product that can be isolated does not separate in solid form the residue can be separated by a chromatographic process after evaporation of the solvent. Gel chromatography with water as eluant has proved to be particularly suitable, since the claimed compounds are eluted as a first fraction according to the size of their molecules, while the unreacted starting products have longer retention times and can be recovered separately.

The composition of the amido oligosaccharides obtained is supported by $^{13}$C-NMR-spectroscopic data.

DETAILED DESCRIPTION OF EMBODIMENTS OF THE INVENTION

Example 1

Reaction of glucamine with gluconic acid lactone

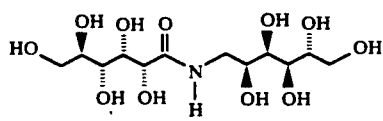

5.3 g (30 mmol) each of glucamine and gluconic acid lactone were dissolved together in 100 ml of anhydrous methanol by heating. The reaction mixture was heated for about 8 h under reflux, and crystalline disaccharide precipitated after a few hours. The precipitate was filtered off with suction, washed with cold methanol and dried under vacuum at 40° C. The yield amounted to 8 g (76%). The melting point was found to be 145°-148° C. and the optical rotation $[\alpha]^{20} \times 12$ (c=1; H$_2$O).

Example 2

Reaction of mannamine with glucopyranosyl arabonic acid lactone

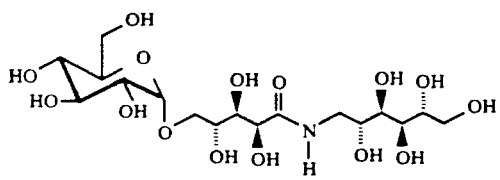

0.5 g (3.0 mmol) of mannamine and 1 g (3.0 mmol) of glucopyranosyl arabonic acid were dissolved together in ml of anhydrous methanol and heated under reflux. After a reaction time the colorless crystals of the trisaccharides were filtered off under vacuum, recrystallized from hot methanol and dried under vacuum at 40° C. The yield amounted to 0.7 g (47%). The melting point was found to be 191°-195° C. and the optical rotation $[\alpha]^{20} = +22$ (c=0.5; H$_2$O).

Example 3

Reaction of isomaltamine (mannite-siomers) with glucopyranosyl arabonic acid lactone

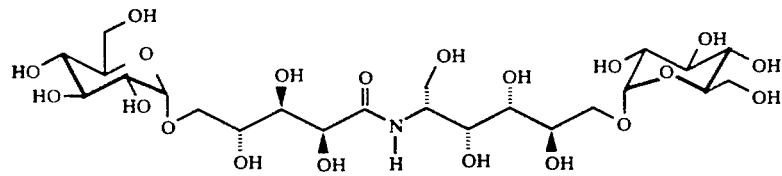

15 g (50 mmol) of isomaltamine (mannite-isomers) and 12.4 g (40 mmol) of glucopyranosyl arabonic acid lactone were dissolved together in 100 ml of dimethyl formamide and stirred for 5 h at 100° C. The reaction mixture was evaporated to dryness under vacuum.

The tetrasaccharide was separated by gel chromatography. After concentration and drying a non-crystalline foam was obtained. The yield amounted to 13.2 g (46%). The melting point was found to be 70°-72° C. and the optical rotation $[\alpha]^{20} = +96$ (c=1; H$_2$O).

What is claimed is:

1. Amido-linked oligosaccharide alditols having the formula

wherein:
$R_1$ = the alditol portion of a mono-, di- or oligosaccharide alditol, in which the alditol portion has 2 to 6 carbon atoms,
$R_2$ = the alditol portion of a mono-, di- or oligosaccharide alditol, in which the alditol portion has 3 to 7 carbon atoms and is combined with the terminal or another carbon atom.

2. Amido-linked oligosaccharide alditols according to claim 1, having the formula

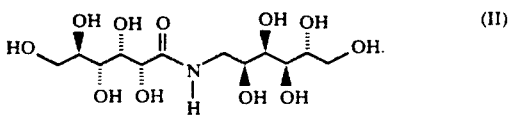

3. Amido-linked oligosaccharide alditols according to claim 1, having the formula

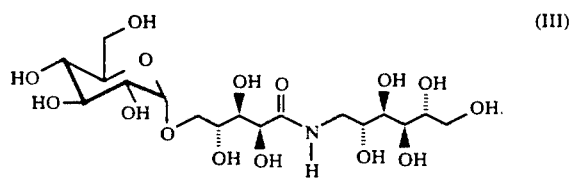

4. Amido-linked oligosaccharide alditols according to claim 1 having the formula

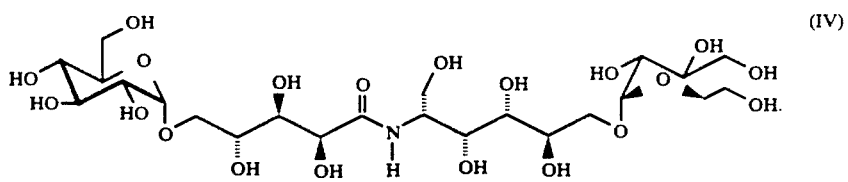

5. A process for the manufacture of oligosaccharide alditols having the formula set forth in claim 1 wherein $R_1$ and $R_2$ are as defined in claim 1 in which amino polyols obtained from reducing mono-,di-or oligosaccharides by reductive amination are N-acylated in a solvent with an anhydride, ester, acid halide or lactone of a sugar acid at temperatures between 20° C. and 120° C.

6. A process according to claim 5, wherein the sugar acid is gluconic acid, arabonic acid or glucopyranosyl arabonic acid.